US00PP19049P3

(12) United States Plant Patent
Layt

(10) Patent No.: US PP19,049 P3
(45) Date of Patent: Jul. 29, 2008

(54) *LOMANDRA CONFERTIFOLIA* PLANT NAMED 'SIR5'

(50) Latin Name: *Lomandra confertifolia*
Varietal Denomination: SIR5

(76) Inventor: Todd Anthony Layt, P.O. Box 1011, Richmond NSW 2753 (AU)

( * ) Notice: Subject to any disclaimer, the term of this patent is extended or adjusted under 35 U.S.C. 154(b) by 137 days.

(21) Appl. No.: 11/353,924

(22) Filed: Feb. 13, 2006

(65) Prior Publication Data

US 2006/0185050 P1 Aug. 17, 2006

Related U.S. Application Data

(60) Provisional application No. 60/652,577, filed on Feb. 14, 2005.

(51) Int. Cl.
*A01H 5/00* (2006.01)

(52) U.S. Cl. ..... Plt./373

(58) Field of Classification Search ..... Plt./263, Plt./373, 384
See application file for complete search history.

(56) References Cited

PUBLICATIONS

Layt; "Lomandra confertifolia matt rush 'SIR5'" *Plant Varieties Journal* 17 (1):29, 135 (Apr. 28, 2004).

Layt; "Lomandra confertifolia matt rush 'SIR5'" *Plant Varities Journal* 18 (1): 83178–180 (May 3, 2005).

*Primary Examiner*—Howard J Locker

(57) ABSTRACT

'SIR5' is a distinctive variety of *Lomandra confertifolia* which is characterized by the combination of its compact habit, shorter leaf blade, and the very glaucous texture of the leaf blade, which gives the foliage color an overall grey-green appearance.

2 Drawing Sheets

Latin name of the genus and species: The Latin name of the genus and species of the novel variety disclosed herein is *Lomandra confertifolia.*

Variety denomination:

The inventive variety of *Lomandra confertifolia* disclosed herein has been given the variety denomination 'SIR5'.

BACKGROUND OF THE INVENTION

The present invention relates to a new and distinct perennial variety of *Lomandra confertifolia,* which has been given the variety denomination of 'SIR5'. *Lomandra confertifolia* is a species of grass-like plant native to Australia and belonging to the *Xanthorrhoeacea* family. The market class for 'SIR5' is that of an ornamental grass-like plant. 'SIR5' is intended for use in landscaping and as a decorative grass-like plant.

Lineage: The *Lomandra confertifolia* variety 'SIR5' was first discovered as a seedling in January 1998 in an Australian nursery in the state of New South Wales during a routine inspection of large quantities of common *Lomandra confertifolia* production stock. 'SIR5' was selected due to its very glaucous upper side leaf texture.

Asexual reproduction: 'SIR5' was first propagated asexually by division in the state of New South Wales, Australia and has since been asexually propagated by division and micropropagation. The distinctive characteristics of the inventive 'SIR5' variety have remained stable and true to type through successive cycles of asexual propagation.

SUMMARY OF THE INVENTION

'SIR5' is a distinctive variety of *Lomandra confertifolia,* which is characterized by the combination of its compact growth habit, shorter leaf blade, and the very glaucous texture of the leaf blade, which gives the foliage color an overall grey-green appearance.

DETAILED BOTANICAL DESCRIPTION OF THE PLANT

The following is a detailed botanical description of a new and distinct variety of a *Lomandra confertifolia* ornamental grass-like plant known as 'SIR5'. Unless indicated otherwise, plant observations were made on 16-month-old plants grown in New South Wales, Australia in nursery pots and field plots. Color notations are based on The Royal Horticultural Society Colour Chart, The Royal Horticultural Society, London, 1995 edition.

Those skilled in the art will appreciated that certain characteristics will vary with older or, conversely younger plants. 'SIR5' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like.

'SIR5' is a perennial, dioecious (male-only), *Lomandra confertifolia* plant, which is a seedling selection from common *Lomandra confertifolia.* After its selection, 'SIR5' was asexually propagated by division. 'SIR5' has an overall foliage color that appears to be grey-green due to a very glaucous leaf texture. The glaucous leaf texture and grey-green coloration are unusual for *Lomandra confertifolia* plants, which usually have weak leaf glaucosity and an overall yellow-green to green foliage color. The combination of its compact form and glaucous leaf texture makes 'SIR5' an attractive ornamental grass-like plant. A botanical description of 'SIR5' and comparisons with other varieties of *Lomandra confertifolia* are provided below.

Technical Description of the Variety.

Figure 1:
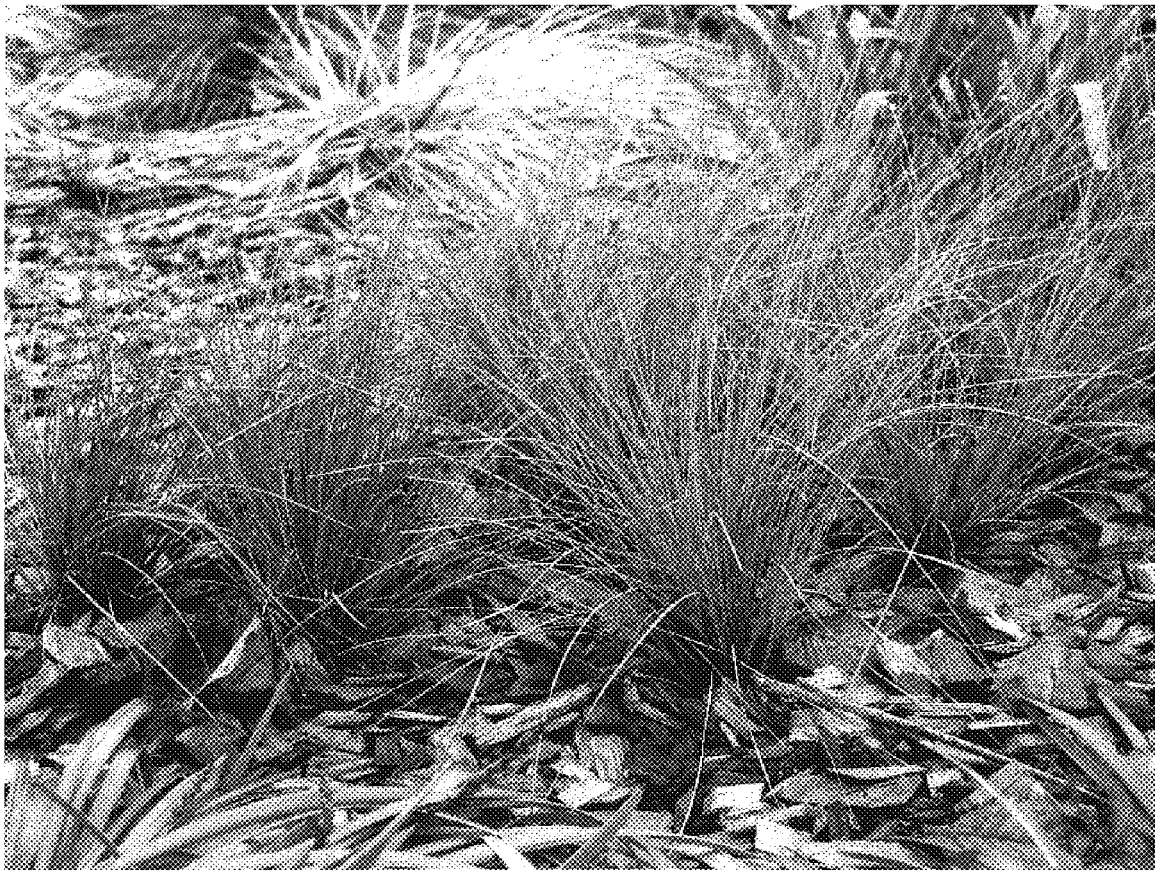
FIG. 1 shows a 'SIR5' plant at about 13 months of age.

Growth Habit: 'SIR5' is a short, rhizomatous plant forming a compact tussock. Average plant height is 35 cm and average plant spread is 45 cm in a mature plant grown in a 140 mm nursery or field pot in Sydney, New South Wales, Australia. A representative *Lomandra confertifolia* 'SIR5' plant is shown in FIG. 1.

Leaves: Width narrow (generally 2 mm), uniform from base to tip, average length 33 cm, upper and lower side color of leaf yellow-green (RHS 147A-B), surface texture strongly glaucous resulting in an overall greyed foliar color approximating grey-green (RHS 189A-B); leaf base cauline; leaf margin entire, leaf blade margins shred at the base, the color of the shredded margin a grey-orange color (RHS 165A); leaf apex dentate; venation pattern parallel, color yellow-green (RHS 147A-B); in cross-section, emerging new leaves flat and mature leaves concave.

*Basal sheath.*—Color brown (RHS 200A) and grey-purple (RHS 187D).

Roots: Fibrous and spreading, similar to other *Lomandra confertifolia.*

Rhizomes: Very short (3 cm to 4 cm); color with leaf sheath removed is white (RHS 155C); surface texture smooth.

Bud: Shape oval, color grey-purple (RHS 183C).

Figure 2:
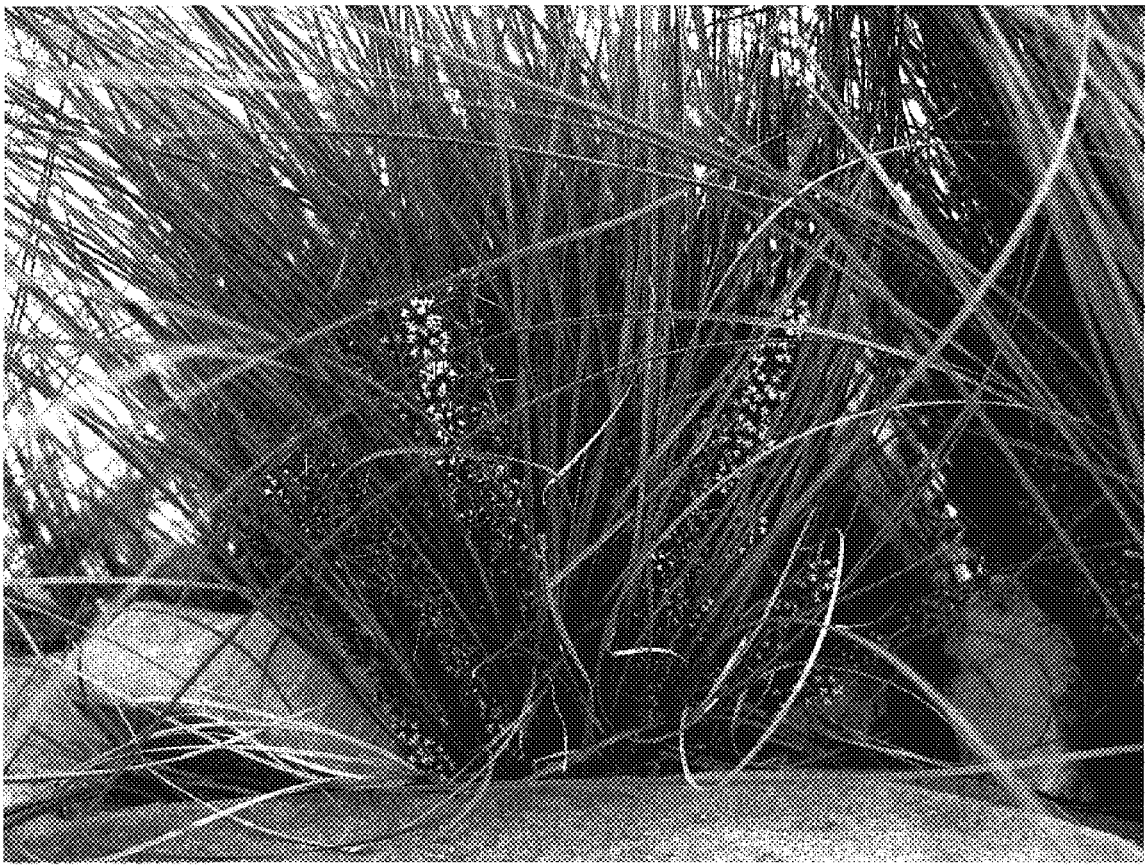
FIG. 2 shows the inflorescence of a 'SIR5' plant.

Inflorescence: Spike (a panicle of clusters), length 50–60 mm, average width 25 mm, composed of male flowers only, predominant color of inflorescence at anthesis yellow (RHS 6A). The inflorescence of *Lomandra confertifolia* 'SIR5' is shown in FIG. 2.

*Floret.*—Sessile, average length 3 mm.

*Pedicels.*—Absent.

*Bracts.*—Average length 6 mm; color grey-brown (approximately RHS 199D).

Flowers: Outer perianth grey-purple (RHS 183C) proximally, yellow green (RHS 146A–B) distally along the central zone, and grey-yellow (RHS 161D) along each perianth segment margin; inner perianth yellow (RHS6A) fading toward the margin to yellow (RHS 13D).

*Flower rachis.*—Length 40–50 mm.

*Reproductive organs.*—Male only, six stamens, anther length 0.5 mm to 0.8 mm, anther color yellow (approximately RHS 8B).

Flowering Period: Primarily in the spring with secondary flowering occurring in summer to autumn in Sydney, New South Wales, Australia, lasting approximately 9 days each period.

Fragrance: Medium strength, typical of *Lomandra confertifolia.*

Seed: Seed not produced.

Environmental Tolerance: 'SIR5' has shown potential for shade tolerance. The winter hardiness of 'SIR5' is at least to zone 8*a* in the Southeastern United States. 'SIR5' has excellent drought tolerance. After severe wilting, 'SIR5' has been noted to recover with watering. 'SIR5' does well in sandy soils, but also tolerates heavy, clay-type soils well.

Disease Resistance: 'SIR5' has good resistance to root rot comparable with most other *Lomandra confertifolia.*

These and other features and characteristics of 'SIR5' are apparent from FIG. 1.

Comparison of 'SIR5' with Other Varieties of *Lomandra confertifolia*

'SIR5' has a compact growth habit with a shorter plant height and a narrower plant diameter and leaves that are shorter than common *Lomandra confertifolia.* The coloration of 'SIR5' is distinct from that of common *Lomandra confertifolia* and another comparable type known as 'Little Con' (unpatented). 'SIR5' has a more glaucous leaf texture resulting in an overall grey-green foliage color, whereas common *Lomandra confertifolia* and 'Little Con' have an overall yellow-green foliage color. Furthermore, 'SIR5' has brown to grey-purple basal shoots with grey-orange shredded margins as compared to 'Little Con', which has yellow-green basal shoots with grey-orange margins and grey-yellow shredded margins. 'SIR5' has a small flower spike typical of *Lomandra confertifolia.*

The novelty and distinctiveness of 'SIR5' as compared with other varieties of *Lomandra confertifolia* is further illustrated in Table 1.

TABLE 1

| Variety | Plant height (cm) | Plant width (cm) | Leaf blade length (cm) | Leaf blade glaucosity | Foliage overall coloration |
|---|---|---|---|---|---|
| 'SIR5' | 35 | 45 | 33 | Strong | Grey-green |
| Common *Lomandra confertifolia* | 42 | 62 | 44 | Weak | Yellow-green |
| 'Little Con' | 26 | 34 | 22 | Weak | Yellow-green |

Test Plots were planted in September 2004, at Abulk Nursery in Windsor, New South Wales, Australia by Abulk Pty Ltd.

That which is claimed is:

1. A new and distinct variety of *Lomandra confertifolia* plant named 'SIR5', substantially as described and illustrated herein.

* * * * *